(12) United States Patent
Daly

(10) Patent No.: US 7,611,502 B2
(45) Date of Patent: Nov. 3, 2009

(54) CONNECTOR FOR ENTERAL FLUID DELIVERY SET

(75) Inventor: Paul J. Daly, Co. Offaly (IE)

(73) Assignee: Covidien AG (CH)

( * ) Notice: Subject to any disclaimer, the term of this patent is extended or adjusted under 35 U.S.C. 154(b) by 575 days.

(21) Appl. No.: 11/254,520

(22) Filed: Oct. 20, 2005

(65) Prior Publication Data

US 2007/0093775 A1  Apr. 26, 2007

(51) Int. Cl.
*A61M 5/32* (2006.01)
(52) U.S. Cl. .................. 604/411; 604/403; 604/412; 604/413; 604/414; 215/247; 215/248; 215/249
(58) Field of Classification Search ............ 604/403, 604/411–414; 215/247–249
See application file for complete search history.

(56) References Cited

U.S. PATENT DOCUMENTS

| | | | |
|---|---|---|---|
| 3,467,270 A | 9/1969 | Eady |
| 3,542,240 A | 11/1970 | Solowey |
| 3,783,895 A | 1/1974 | Weichselbam |
| 3,938,520 A | 2/1976 | Scislowicz et al. |
| 4,547,192 A | 10/1985 | Brodsky et al. |
| 4,613,323 A | 9/1986 | Norton et al. |
| 4,655,763 A | 4/1987 | Malcolm et al. |
| 4,683,424 A | 7/1987 | Cutright et al. |
| 4,688,595 A | 8/1987 | Srebnik et al. |
| 4,698,059 A | 10/1987 | Johnson |
| 4,699,296 A | 10/1987 | Schrock, Jr. |
| 4,713,064 A | 12/1987 | Bruno et al. |
| 4,754,891 A | 7/1988 | Srebnik et al. |
| 4,781,704 A | 11/1988 | Potter |
| 4,787,890 A | 11/1988 | Ufermann |
| 4,826,500 A | 5/1989 | Rautsola |
| 4,828,550 A | 5/1989 | Kurimoto |
| 4,834,744 A | 5/1989 | Ritson |
| 4,863,424 A | 9/1989 | Blake, III et al. |
| 4,869,725 A | 9/1989 | Schneider et al. |
| 4,871,359 A | 10/1989 | Sjönell |
| 4,886,504 A | 12/1989 | Arvidson et al. |
| 4,888,008 A | 12/1989 | D'Alo et al. |

(Continued)

FOREIGN PATENT DOCUMENTS

| | | |
|---|---|---|
| DE | 86 16 731 U1 | 1/1987 |
| DE | 19807131 A1 | 8/1999 |
| DE | 19842960 A1 | 3/2000 |
| DE | 200 17 609 U1 | 1/2001 |
| DE | 20017609 U1 | 1/2001 |

(Continued)

OTHER PUBLICATIONS

Machine-generated English language translation of EP0355795 provided by esp@cenet.*

(Continued)

*Primary Examiner*—Tatyana Zalukaeva
*Assistant Examiner*—Ilya Y Treyger

(57) ABSTRACT

A connector for use in connecting a container of liquid nutrients to an enteral feeding tube to supply the liquid nutrients to a patient includes an integrally formed spike projecting into a cavity defined by an interior surface of a body of the connector. An air passage in communication with the cavity extends through the spike to outside the connector. A filter is secured to the end of the passage outside the connector. The body of the connector is free of structure that both defines any portion of the liquid passage and is formed for penetrating the puncturable seal of the container.

15 Claims, 9 Drawing Sheets

U.S. PATENT DOCUMENTS

| | | | |
|---|---|---|---|
| 4,895,275 A | 1/1990 | Quinn et al. |
| 4,909,797 A | 3/1990 | Timothy |
| 4,919,649 A | 4/1990 | Timothy et al. |
| 4,934,545 A | 6/1990 | Pezzoli et al. |
| 4,940,399 A | 7/1990 | Gorton et al. |
| 4,951,845 A | 8/1990 | Pezzoli et al. |
| 4,969,565 A | 11/1990 | Justal et al. |
| 4,997,429 A | 3/1991 | Dickerhoff et al. |
| 5,041,105 A | 8/1991 | D'Alo et al. |
| 5,057,093 A | 10/1991 | Clegg et al. |
| 5,088,995 A | 2/1992 | Packard et al. |
| 5,122,123 A | 6/1992 | Vaillancourt |
| 5,125,522 A | 6/1992 | Pezzoli et al. |
| 5,125,897 A | 6/1992 | Quinn et al. |
| 5,137,527 A | 8/1992 | Miller et al. |
| 5,188,628 A | 2/1993 | Rani et al. |
| 5,242,429 A | 9/1993 | Nwaneri et al. |
| 5,267,983 A | 12/1993 | Oilschlager et al. |
| 5,290,250 A | 3/1994 | Bommarito |
| 5,314,405 A | 5/1994 | Kriesel et al. |
| 5,332,113 A | 7/1994 | Kusler, III et al. |
| 5,336,203 A | 8/1994 | Goldhardt et al. |
| 5,372,578 A | 12/1994 | Kriesel et al. |
| 5,411,491 A | 5/1995 | Goldhardt et al. |
| 5,437,655 A | 8/1995 | Bartholomew |
| 5,458,583 A | 10/1995 | McNeely et al. |
| 5,468,226 A | 11/1995 | Kriesel |
| 5,492,533 A | 2/1996 | Kriesel |
| 5,498,253 A | 3/1996 | Aswad et al. |
| 5,569,209 A | 10/1996 | Roitman |
| 5,569,222 A | 10/1996 | Haselhorst et al. |
| 5,586,590 A * | 12/1996 | Venooker et al. ............. 141/386 |
| 5,620,433 A | 4/1997 | Aswad et al. |
| 5,645,538 A | 7/1997 | Richmond |
| 5,665,064 A | 9/1997 | Bodicky et al. |
| 5,681,294 A | 10/1997 | Osborne et al. |
| 5,693,019 A | 12/1997 | Kriesel |
| 5,716,347 A | 2/1998 | Gibbs et al. |
| 5,720,734 A | 2/1998 | Copenhaver et al. |
| 5,730,418 A | 3/1998 | Feith et al. |
| 5,735,841 A | 4/1998 | Bourguignon et al. |
| 5,752,511 A | 5/1998 | Simmons et al. |
| 5,772,255 A | 6/1998 | Osborne et al. |
| 5,776,117 A | 7/1998 | Haselhorst et al. |
| 5,782,383 A | 7/1998 | Robinson |
| 5,836,924 A | 11/1998 | Kelliher et al. |
| 5,840,065 A | 11/1998 | Goldhardt et al. |
| 5,891,129 A | 4/1999 | Daubert et al. |
| 5,895,373 A | 4/1999 | Hirsch et al. |
| 5,924,584 A | 7/1999 | Hellstrom et al. |
| 5,925,011 A | 7/1999 | Faict et al. |
| 5,954,104 A | 9/1999 | Daubert et al. |
| 5,988,700 A | 11/1999 | Rrichard |
| 6,012,596 A | 1/2000 | Oglesbee et al. |
| 6,056,724 A | 5/2000 | Lacroix |
| 6,066,112 A | 5/2000 | Quinn |
| 6,068,617 A | 5/2000 | Richmond |
| 6,098,795 A | 8/2000 | Mollstam et al. |
| 6,139,534 A | 10/2000 | Niedospial |
| 6,165,168 A | 12/2000 | Russo |
| 6,173,199 B1 | 1/2001 | Gabriel |
| 6,182,698 B1 | 2/2001 | Barak |
| 6,183,465 B1 | 2/2001 | Meier et al. |
| 6,319,243 B1 | 11/2001 | Becker et al. |
| 6,332,467 B1 | 12/2001 | Hutson et al. |
| 6,364,143 B1 | 4/2002 | Knierbein |
| 6,371,319 B2 | 4/2002 | Yeaton et al. |
| 6,375,231 B1 | 4/2002 | Picha et al. |
| 6,394,993 B1 | 5/2002 | Chang et al. |
| 6,409,708 B1 | 6/2002 | Wessman |
| 6,471,676 B1 | 10/2002 | DeLegge et al. |
| 6,503,240 B1 | 1/2003 | Niedospial, Jr. et al. |
| 6,524,295 B2 | 2/2003 | Daubert et al. |
| 6,551,299 B2 | 4/2003 | Miyoshi et al. |
| 6,568,439 B1 | 5/2003 | Se et al. |
| 6,506,179 B1 | 6/2003 | Tiefenthal et al. |
| 6,582,395 B1 | 6/2003 | Burkett et al. |
| 6,610,041 B2 | 8/2003 | Daubert et al. |
| 6,635,043 B2 | 10/2003 | Daubert et al. |
| 6,652,509 B1 | 11/2003 | Helgren et al. |
| 6,659,976 B2 | 12/2003 | Beck et al. |
| 6,678,553 B2 | 1/2004 | Lerner et al. |
| 6,709,424 B1 | 3/2004 | Knierbein |
| 6,752,790 B2 | 6/2004 | Coombs |
| 6,767,340 B2 | 7/2004 | Willis et al. |
| 6,769,539 B2 | 8/2004 | Stern et al. |
| 6,808,521 B1 | 10/2004 | McMichael |
| 6,852,094 B2 | 2/2005 | Beck et al. |
| 6,875,204 B1 * | 4/2005 | Hopkins et al. ............. 604/414 |
| 6,875,205 B2 | 4/2005 | Leinsing |
| 6,960,199 B2 | 11/2005 | Burkett et al. |
| 6,971,548 B2 | 12/2005 | Smith |
| 7,063,690 B2 | 6/2006 | Kessler et al. |
| 7,080,672 B2 | 7/2006 | Fournie et al. |
| 7,462,170 B2 | 12/2008 | Fournie et al. |
| 2001/0000793 A1 | 5/2001 | Daubert et al. |
| 2003/0006159 A1 | 1/2003 | Thorball et al. |
| 2003/0073971 A1 | 4/2003 | Saker |
| 2003/0075469 A1 | 4/2003 | Herbert |
| 2003/0088232 A1 | 5/2003 | Duell |
| 2003/0191426 A1 | 10/2003 | Lerner et al. |
| 2003/0212381 A1 | 11/2003 | Whitehead, III |
| 2003/0216713 A1 | 11/2003 | Kessler et al. |
| 2004/0011760 A1 | 1/2004 | Schupp et al. |
| 2004/0044327 A1 | 3/2004 | Hasegawa |
| 2004/0054350 A1 | 3/2004 | Shaughnessy et al. |
| 2004/0104246 A1 | 6/2004 | Kawaguchi et al. |
| 2004/0146341 A1 | 7/2004 | Sundheimer et al. |
| 2004/0153047 A1 | 8/2004 | Blank et al. |
| 2004/0193115 A1 | 9/2004 | Itrich et al. |
| 2004/0249350 A1 | 12/2004 | Rani |
| 2005/0033245 A1 | 2/2005 | Abrahamson et al. |
| 2005/0033267 A1 | 2/2005 | Decaria |
| 2005/0033268 A1 | 2/2005 | Decaria |
| 2005/0033269 A1 | 2/2005 | Decaria |
| 2005/0036831 A1 | 2/2005 | Sundheimer et al. |
| 2005/0041888 A1 | 2/2005 | Matsuzawa et al. |
| 2005/0063847 A1 | 3/2005 | Fathallah et al. |
| 2005/0087553 A1 | 4/2005 | Halfacre et al. |

FOREIGN PATENT DOCUMENTS

| | | |
|---|---|---|
| DE | 200 17 609 U1 | 2/2001 |
| EP | 0119373 A1 | 9/1984 |
| EP | 0281270 B1 | 9/1988 |
| EP | 0355795 A1 | 2/1990 |
| EP | 0376 629 | 3/1995 |
| EP | 0711538 B1 | 5/1996 |
| EP | 0729761 A | 9/1996 |
| EP | 0792631 A1 | 9/1997 |
| EP | 1010412 A2 | 6/2000 |
| EP | 1027900 A1 | 8/2000 |
| EP | 1384466 A1 | 1/2004 |
| WO | 9320772 | 10/1993 |
| WO | 9504564 | 2/1995 |
| WO | 9513105 | 5/1995 |
| WO | 2004084793 A1 | 10/2004 |

OTHER PUBLICATIONS

English language abstract of EP0355795 from esp@cenet.*
Office action dated Apr. 2, 2009 from related U.S. Appl. No. 11/561,283, 10 pages.

* cited by examiner

CONNECTOR FOR ENTERAL FLUID DELIVERY SET

BACKGROUND OF THE INVENTION

The present invention relates generally to a connector for an enteral fluid delivery set, and more particularly, to such a connector having an air passage extending through an integrally formed spike.

In an enteral fluid delivery set for a patient, there is a need to provide a connector that will effect a quick connection of a fluid delivery set to a prefilled, foil-sealed container containing enteral nutritional fluid. In such systems, the connector is preferably in the form of a cap, which replaces the shipping cap on the prefilled container. Either the cap or the enteral fluid delivery set includes a spiking member for perforating the foil seal on the container. The cap has a liquid passage to fluidly connect the container and a feeding tube of the delivery set and an air passage to introduce air into the container as fluid flows from the container. A filter is placed in the air passage to inhibit microbes from passing into the container.

In one type of a conventional connector, the liquid passage is formed through the spiking member. This arrangement simplifies the setup procedure; however, sometimes portions of the punctured seal may become lodged in the liquid passage when the spike perforates the seal or the seal may fold upward into the passage and inhibit the flow of liquid.

In another type of conventional connector, the air passage does not extend into the interior of the connector, and during use, the entrance of the air passage is adjacent the seal. Some prior spike arrangements do not provide a sufficiently large opening through the foil seal, and the seal may become lodged in the air passage, possibly causing the feed container to implode.

SUMMARY OF THE INVENTION

In one aspect of the present invention, a connector for use in connecting a container of liquid nutrients to an enteral feeding tube to supply the liquid nutrients to a patient generally comprises a body having an interior surface defining a cavity for receiving an outlet of the container, and an exterior surface. A liquid passage is defined in the body. The liquid passage has a first end in fluid communication with the cavity and a second end for connection to the enteral feeding tube to fluidly connect the container and the enteral feeding tube when the connector is received on the container. A spike is formed integrally with the body. The spike has a free end projecting into the cavity for piercing a puncturable seal covering the outlet of the container as the outlet of the container is being received in the cavity. An air passage extends through the spike to the exterior surface of the body for introducing air from outside the connector into the container when the connector is attached to the container. The body is free of structure that both defines any portion of the liquid passage and is formed for penetrating the puncturable seal of the container.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
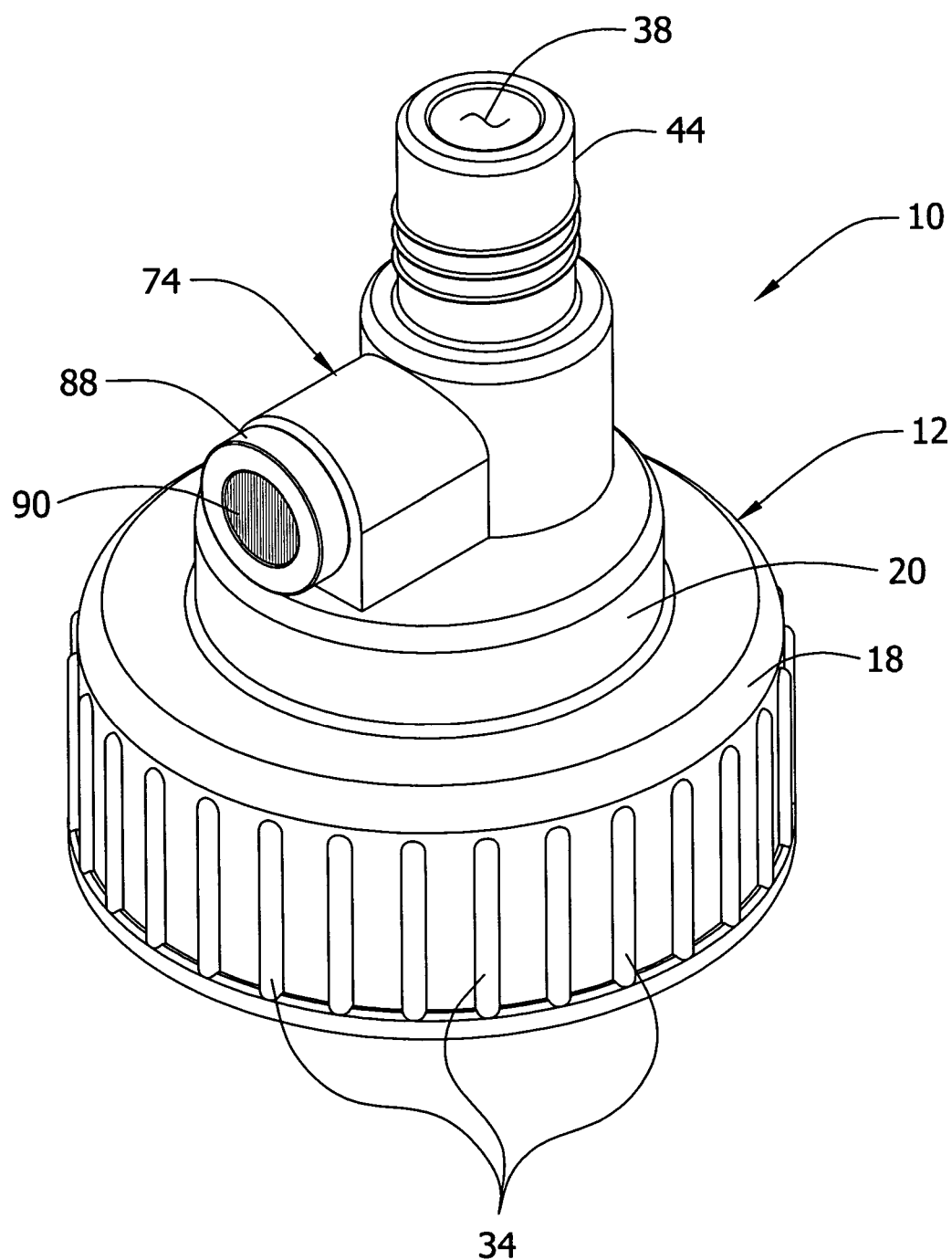
FIG. 1 is a perspective of a connector for connecting an enteral container of liquid nutrients to an enteral feeding tube constructed according to the teachings of the present invention.
Figure 2:
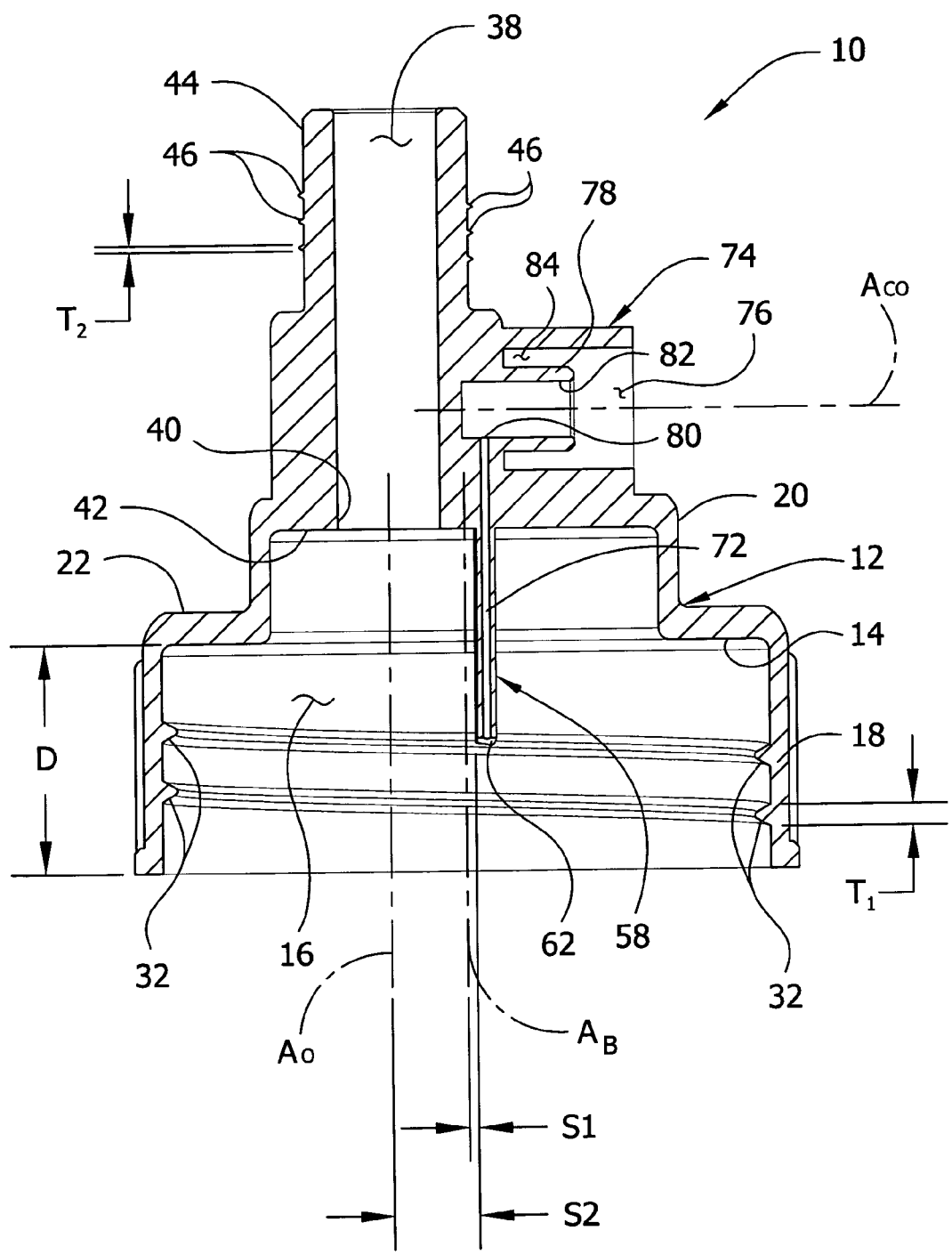
FIG. 2 is a vertical section of the connector.
Figure 3:
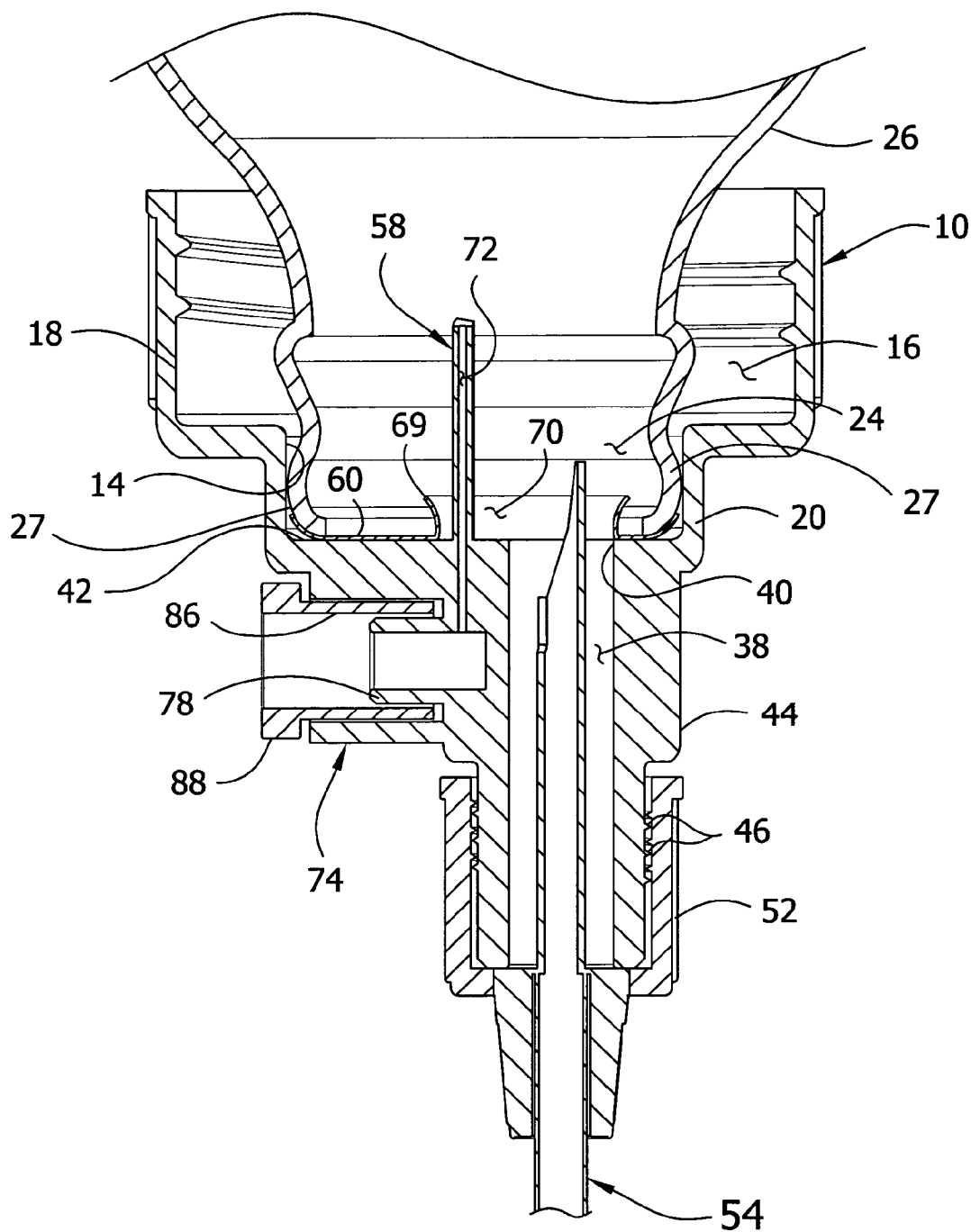
FIG. 3 is a vertical section of the connector snapped into to a small outlet container and attached to an enteral feeding tube.
Figure 4:
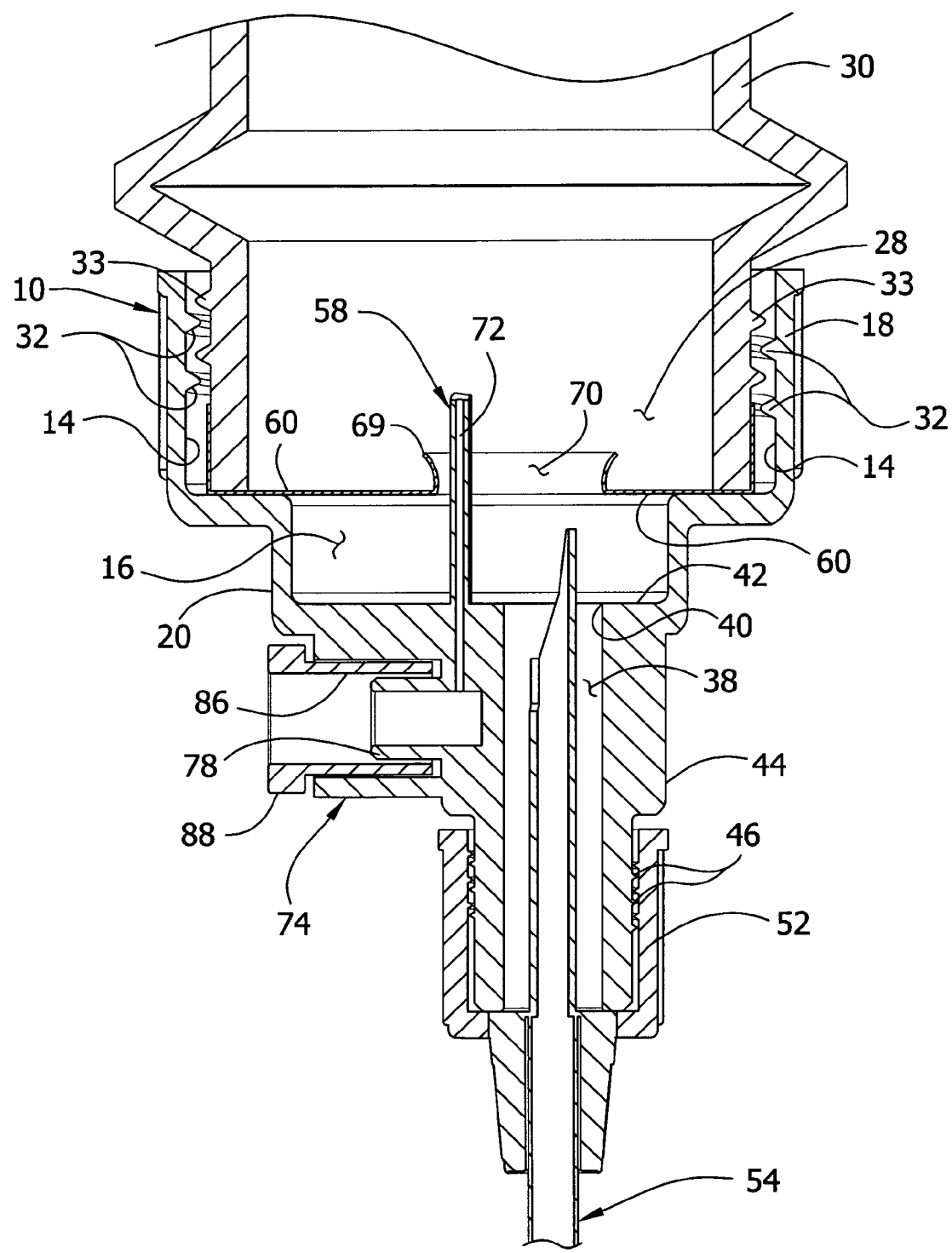
FIG. 4 is a vertical section of the connector threaded onto a large outlet container and attached to an enteral feeding tube.
Figure 5:
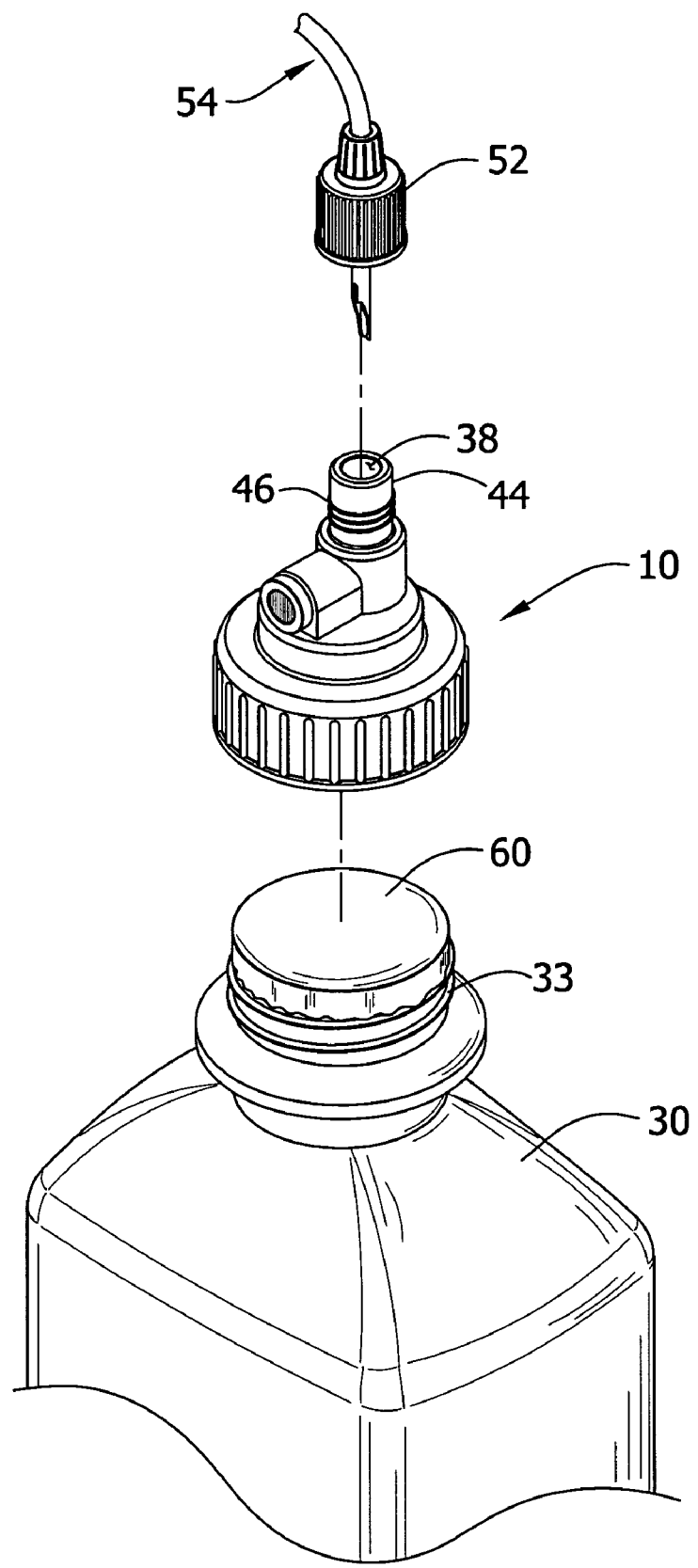
FIG. 5 is fragmentary exploded perspective of the large outlet container, the connector and the enteral feeding tube.

Referring now to the drawings, and in particular to FIGS. 1-2, a connector for connecting a container of liquid nutrients to an enteral feeding tube is generally indicated at 10. The connector includes a body, generally indicated at 12, having an interior surface 14 (FIG. 2) that defines a cavity 16 for receiving an outlet of the container, as explained in more detail below (FIGS. 3-5). The body 12 has a cylindrical lower portion 18 and a smaller cylindrical upper portion 20 projecting upward from a top surface 22 of the lower portion.

Referring to FIGS. 3-5, the cavity 16 is configured for receiving different types of containers. As shown in FIG. 3, the cavity 16 at the upper portion 20 is sized and shaped for snap-fit reception of a relatively small outlet 24 of a container 26. The interior surface 14 at the upper portion 20 is elastically deformable to allow a rigid snap-fit member 27 (e.g., a projecting rim extending around the outlet 24) to snap-fit into the upper portion.

As shown in FIG. 4, the cavity 16 at the lower portion 18 is sized and shaped to threadably receive a relatively larger outlet 28 of a container 30. The interior surface 14 at the lower portion 18 of the connector 10 includes internally projecting threads 32 for attaching to external threads 33 extending around the outlet 28 of the container 30. The depth D (FIG. 2) of the cavity 16 at the lower portion 18 is between about 0.55 inches (1.40 cm) and 0.71 inches (1.80 cm). This depth D allows the connector 10 to attach to containers 30 having necks of different sizes and accommodates a more secure connection with the different containers. Further, the internal threads 32 of the lower portion 18 have a thickness $T_1$ of between about 0.047 inches (0.12 cm) and about 0.043 inches (0.11 cm) to (height). Ridges 34 (FIG. 1) disposed around an exterior surface of the body 12 at the lower portion 18 provide a user with adequate grip when threading the connector 10 on the container 30. The connector 10 may be configured to attach to an outlet of a container in other ways without departing from the scope of this invention. Moreover, the connector 10 may be configured to attach only to one type of container, such as a threaded container or a snap-fit container, or the connector may be configured to attach to more than two types of containers.

Referring to FIGS. 2-4, a liquid passage 38 extends through the upper portion 20 of the body 12 and is in fluid communication with the cavity 16. An opening 40 of the liquid passage 38 is substantially flush with an upper surface section 42 of the interior surface 14 of the body 12 (i.e., the liquid passage does not extend into the cavity 16), although it is contemplated that the liquid passage may extend into the cavity. In the illustrated embodiment, the upper surface section 42 is substantially flat. The liquid passage 38 also extends through a conduit 44 projecting outward from the exterior surface of the body 12 at the upper portion 20. The conduit 44 has externally projecting threads 46 for attaching to an internally threaded adapter 52 of an enteral feeding tube 54 (FIGS. 3-5). The external threads 46 of the conduit 44 have a thickness $T_2$ of between about 0.043 inches (0.11 cm) and about 0.002 inches (0.06 cm). Other ways of connecting the enteral feeding tube 54 to the connector 10, including the use of an interference fitting, is within the scope of this invention.

As shown in FIGS. 3-5, when assembled, the connector 10 is secured to the outlet 24, 28 of the respective container 26, 30 by either threading (as shown in FIGS. 4 and 5) or fitting the connector on the container (FIG. 3). The threaded adapter 52 is threaded on the conduit 44 of the connector 10. Thus, when assembled, the connector 10 fluidly connects the enteral feeding tube 54 to the attached container 26, 30.

Figure 6:
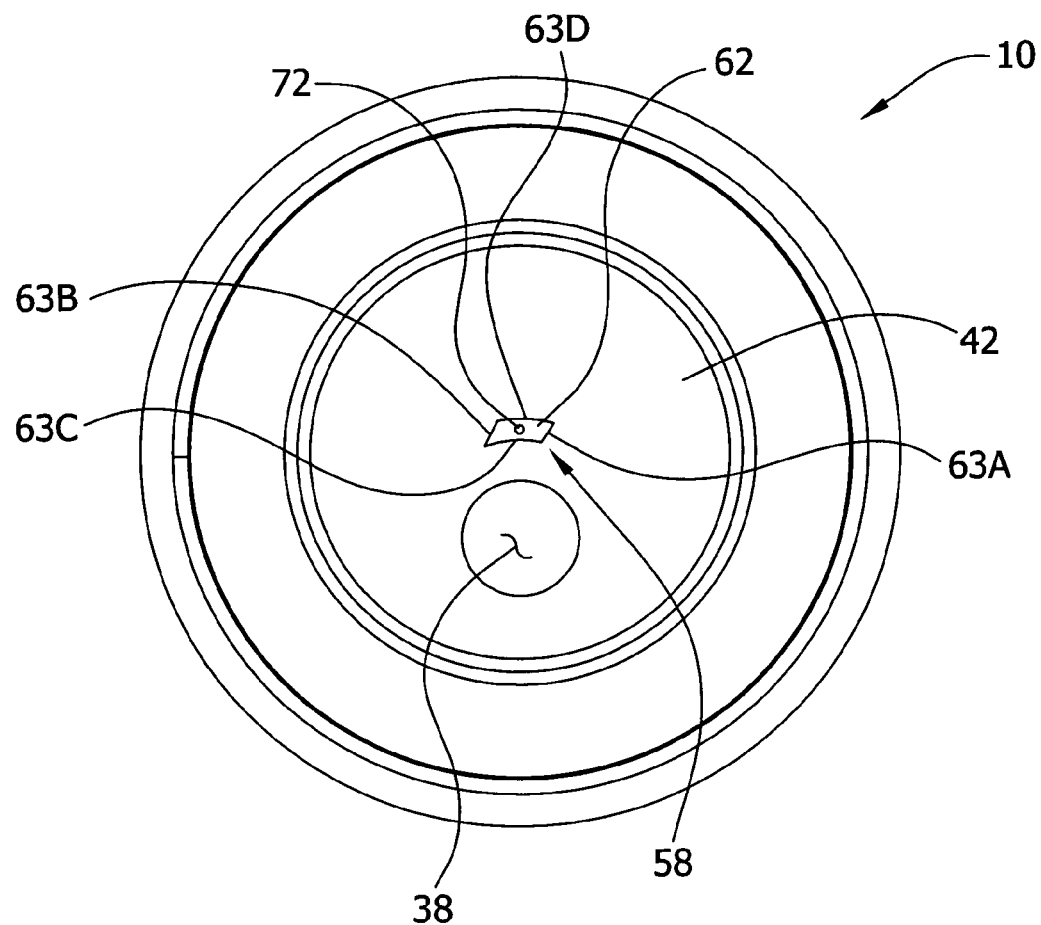
FIG. 6 is a bottom plan view of the connector.
Figure 7:
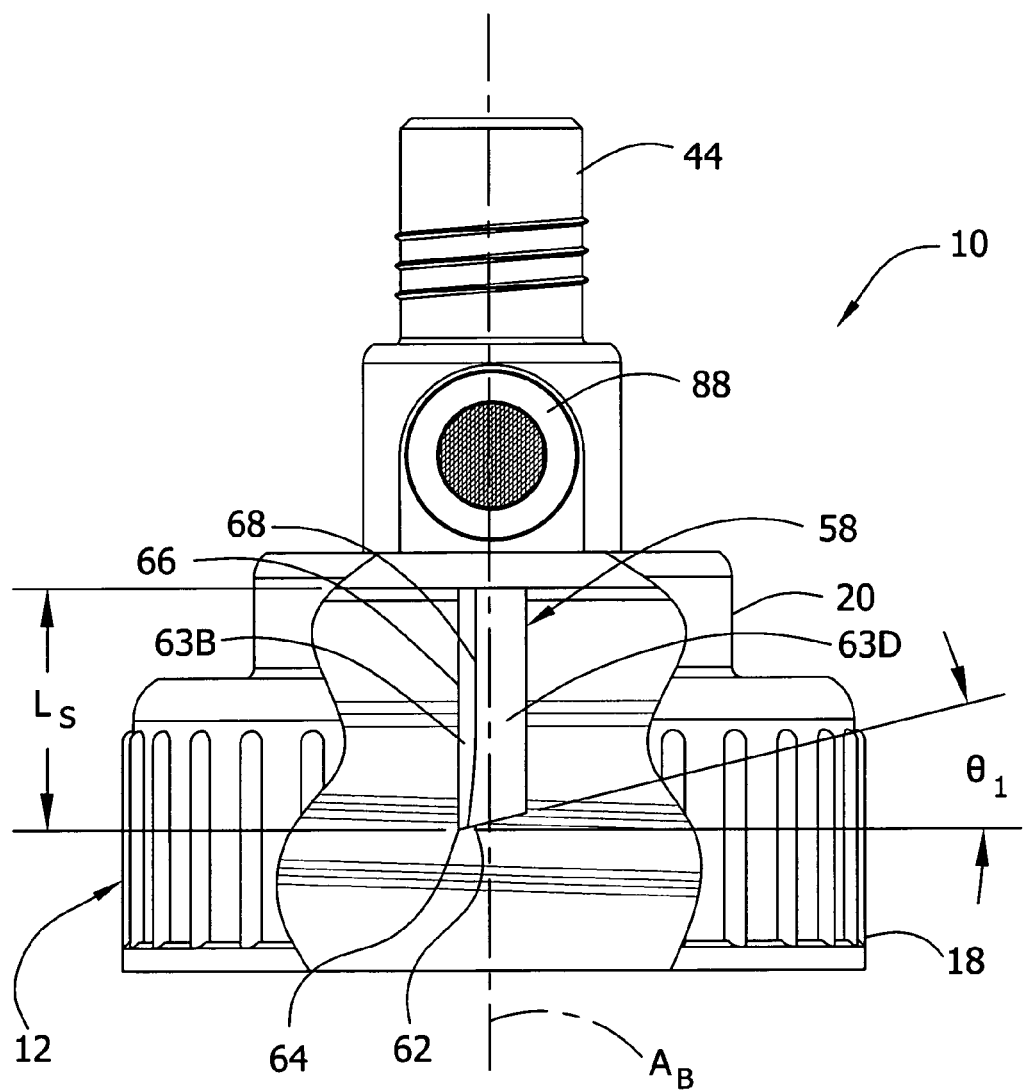
FIG. 7 is a front elevation of the connector with a portion of a body of the connector broken away to reveal a spike of the connector.

Referring to FIGS. 2-7, a generally elongate spike, generally indicated at 58, formed integrally with the body 12 projects from the upper surface section 42 of the body into the cavity 16. The spike 58 is spaced a distance $S_1$ (FIG. 2) from a central axis $A_B$ of the body 12 and a distance $S_2$ (FIG. 2) from a longitudinal axis $A_O$ of the opening 40 of the liquid passage 38. The spike 58 is configured to puncture a puncturable seal 60 (e.g., foil seal) (FIGS. 3-5) covering the outlet 24, 28 of the container 26, 30 to allow the liquid nutrients to exit the container. As shown best in FIG. 6, the spike 58 has a pair of opposite narrow sides 63A, 63B and a pair of opposite broad sides 63C, 63D extending between its length $L_S$ (FIG. 7).

Figure 8:
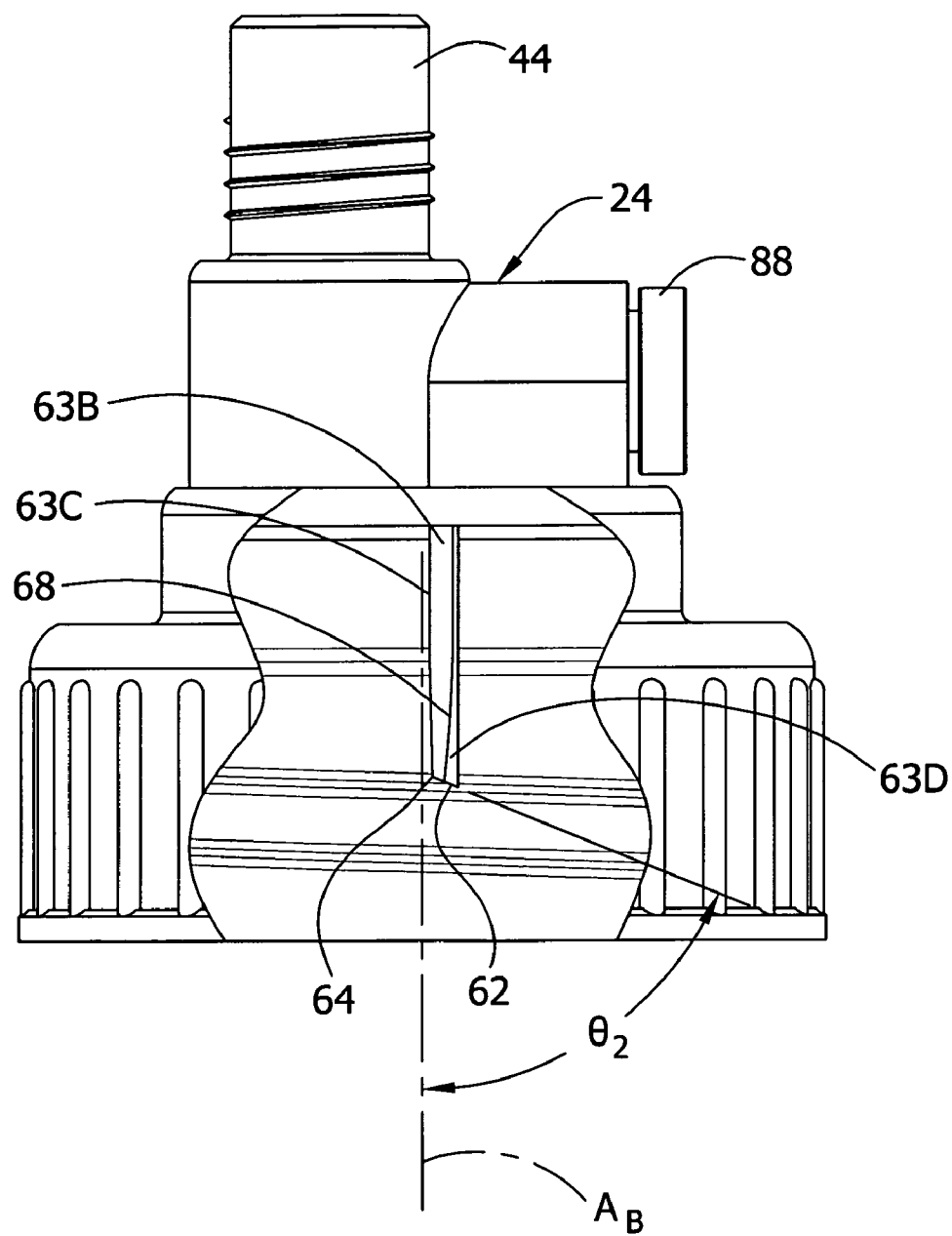
FIG. 8 is a side elevation of the connector with a portion of the body of the connector broken away to reveal the spike.
Figure 9:
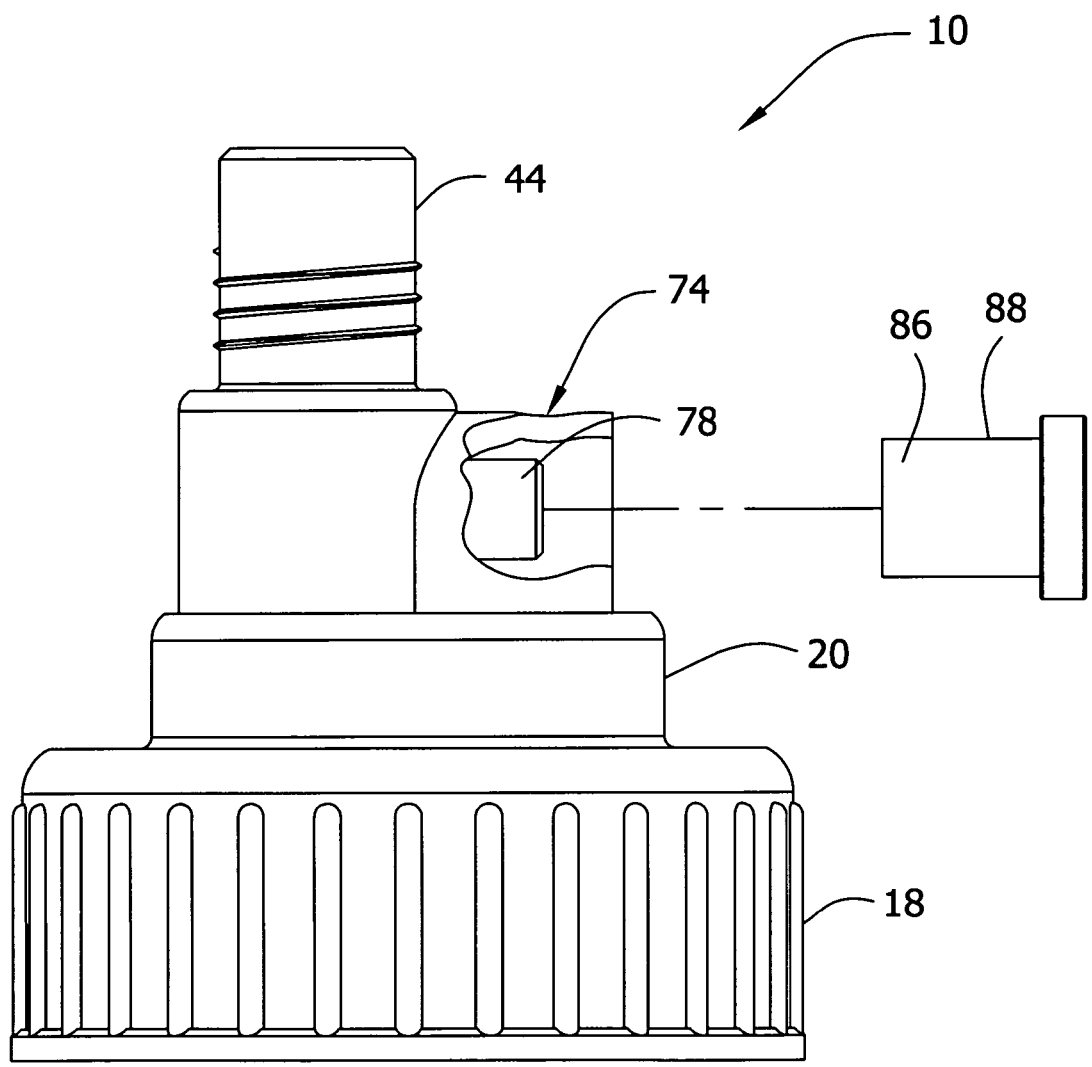
FIG. 9 is a side elevation of the connector with an air filter exploded from the connector and a mount for the filter partially broken to illustrated internal construction.

Referring to FIGS. 6 and 7, a bottom surface 62 of the spike 58 (i.e., at the free end of the spike) is generally flat. As shown in FIG. 7, the bottom surface 62 is beveled from the narrow side 63A (broadly, a first narrow side) to the opposite narrow side 63B (broadly, a second narrow side), such that the bottom surface lies in a plane intersecting the central axis $A_B$ of the body 12 at an angle $\theta_1$. This beveled configuration of the bottom surface 62 forms a sharp tip 64 for puncturing the seal 60 of the threaded container 30. As shown in FIG. 8, the bottom surface 62 is also beveled from the broad side 63C (broadly, a first broad side) to the opposite broad side 63D (broadly, a second broad side), such that the bottom surface lies in a plane intersecting the central axis of the body $A_B$ at an angle $\theta_2$.

Referring to FIG. 7, the narrow side 63B is beveled from the broad side 63D to the opposite broad side 63C, defining a knife edge 66 along the length $L_S$ of the spike to the tip 64. After the seal 60 is punctured by the tip 64, the knife edge 66 cuts the seal 60 as the connector 10 is rotated (e.g., threaded) on the outlet 24, 28 of the container 26, 30. The spike 58 makes a relatively large (i.e., larger than the width of the spike 58), generally circular opening 70 through the seal, as illustrated in FIGS. 3 and 4.

Referring to FIGS. 6-8, the broad side 63D of the spike 58 is generally arcuate and joins the beveled narrow side 63B at folding edge 68. The narrow side 63B tapers toward the bottom surface 62 such that the folding edge 68 falls off or angles toward the tip 64. As the connector 10 is rotated on the container 26, 30, the knife edge 66 cuts the seal 60 and forms a foil edge margin 69 (FIGS. 3 and 4) defining the opening 70. Referring to FIGS. 3 and 4, as the connector 10 continues to rotate, the folding edge 68 of the spike 58 folds the foil edge margin 68 of the seal 60 away from the opening 70 in the seal 60 and away from the opening 40 of the liquid passage 38 so that the foil edge margin will not obstruct the openings.

Referring to FIGS. 2-4, an air passage 72 extends from the cavity 16 through the spike 58 and the upper portion 20 of the body 12. A vacuum within the container 26, 30, created when the liquid exits the container, draws air into the container through the air passage 72, thereby allowing the liquid to flow continuously and freely out of the container through the liquid passage 38 of the connector 10. The air passage 72 opens at the bottom surface 62 of the spike 58 to communicate with the cavity 16, although the passage may open at other locations along the length $L_S$ of the spike.

Referring to FIGS. 2-4 and 9, the air passage 72 is fluidly connected to a filter mount, generally indicated at 74, projecting outward from the exterior surface of the body 12 at the upper portion 20. The filter mount 74 includes a large cylindrical opening 76 (FIG. 2) having a longitudinal axis $A_{CO}$ extending generally transverse to the central axis $A_B$ of the body 12. A tubular duct 78 disposed within the large opening 76 extends generally coaxially therein. As shown in FIG. 2, the duct 78 has a first open end 80 in fluid communication with the air passage 72 and a second open end 82 terminating within the large opening 76. The large opening 76 and an exterior surface of the duct 78 define an annular socket 84 (FIG. 2) making an interference fit with a tubular end 86 of a filter 88 (FIG. 9) such that the filter is in fluid communication with the duct and the air passage 72 when fitted in the socket. As shown in FIGS. 1, 3 and 4, when the air filter 88 is received in the filter mount 74, a filter medium 90 of the filter extends outside the mount.

The entire connector 10, excluding the air filter 88, may be formed as a homogeneous and integral unit, such as by molding (e.g., injection molding) or by forming, including boring, from stock material. Alternatively, the connector 10 may be constructed of one or more separate components fastened together in a suitable manner. Suitable materials for making the connector 10 include polypropylene (e.g., polypropylene 535), polyethylene and other suitable polymers. Other material may be used, and different material may be used for the separate components of the connector 10.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A connector for use in connecting a container of liquid nutrients to an enteral feeding tube to supply the liquid nutrients to a patient, the connector comprising:

a body having an interior surface defining a cavity for receiving an outlet of the container, and an exterior surface;

a liquid passage defined in the body having a first end in fluid communication with the cavity and a second end for connection to the enteral feeding tube to fluidly connect the container and the enteral feeding tube when the connector is received on the container;

a spike formed integrally with the body and having a free end projecting into the cavity for piercing a puncturable seal covering the outlet of the container as the outlet of the container is being received in the cavity, the spike further comprising a generally flat bottom surface and having a knife edge substantially along its length;

an air passage extending through the spike to the exterior surface of the body, the air passage opens at the flat bottom surface of the spike for introducing air from outside the connector into the container when the connector is attached to the container; and the cavity being free of structure that defines any portion of the liquid passage and the spike is formed for penetrating the puncturable seal of the container.

2. A connector as set forth in claim 1 wherein no portion of the liquid passage extends into the cavity.

3. A connector as set forth in claim 2 wherein the interior surface of the body includes an upper surface section, the liquid passage having an opening generally flush with the upper surface section.

4. A connector as set forth in claim 3 wherein the spike projects from the interior surface of the body.

5. A connector as set forth in claim 4 wherein the spike is spaced from the liquid passage opening on the interior surface.

6. A connector as set forth in claim 3 wherein the upper surface section is substantially flat.

7. A connector as set forth in claim 1 further comprising an air filter and a filter mount disposed on the exterior surface of the body in fluid communication with the air passage for connecting the air filter to the body.

8. A connector as set forth in claim 1 wherein the body has a cylindrical lower portion and a cylindrical upper portion projecting from the lower portion, the interior surface at the lower portion having internally projecting threads for threadably attaching to a container with a threaded, larger diameter outlet, the interior surface at the upper portion being adapted for snap fitting to a container with a smaller diameter outlet.

9. A connector as set forth in claim 8 wherein the liquid passage is partially defined by a tubular conduit projecting outward from the exterior surface of the upper portion of the body and having threads on its exterior surface for threadable attachment to the enteral feeding tube.

10. A connector as set forth in claim 1 wherein the bottom surface of the spike lies generally in a plane intersecting a central axis of the body at an angle thereby to form a tip at a lower end of the knife edge.

11. A connector as set forth in claim 1 wherein the body has a central axis, the spike being spaced from the central axis.

12. A connector as set forth in claim 11 wherein the liquid passage has an opening in its first end having a longitudinal axis spaced from the central axis of the body.

13. A connector for use in connecting a container of liquid nutrients to an enteral feeding tube to supply the liquid nutrients to a patient, the connector comprising:

a body having an interior surface defining a cavity for receiving an outlet of the container, and an exterior surface;

a liquid passage defined in the body having a first end in fluid communication with the cavity and a second end for connection to the enteral feeding tube to fluidly connect the container and the enteral feeding tube when the connector is received on the container;

a spike formed integrally with the body and having a free end projecting into the cavity for piercing a puncturable seal covering the outlet of the container as the outlet of the container is being received in the cavity;

an air passage extending through the spike to the exterior surface of the body for introducing air from outside the connector into the container when the connector is attached to the container; and the cavity being free of structure that defines any portion of the liquid passage and the spike is formed for penetrating the puncturable seal of the container, wherein the spike comprises first and second opposite broad sides, and first and second opposite narrow sides, the second narrow side being beveled from the second broad side to the first broad side, so that a cutting edge is formed where the second narrow side meets the first broad side, the second narrow side tapering toward the free end of the spike such that a folding edge is formed where the second narrow side meets the second broad side.

14. A connector as set forth in claim 13 wherein the first broad side is generally arcuate.

15. A connector as set forth in claim 13 wherein a folding edge of the spike folds an edge of the seal away from opening of the liquid passageway for preventing the seal from blocking the flow of fluid from container.

* * * * *

UNITED STATES PATENT AND TRADEMARK OFFICE
CERTIFICATE OF CORRECTION

PATENT NO. : 7,611,502 B2  Page 1 of 1
APPLICATION NO. : 11/254520
DATED : November 3, 2009
INVENTOR(S) : Paul J. Daly It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 701 days.

Signed and Sealed this

Twelfth Day of October, 2010

David J. Kappos
*Director of the United States Patent and Trademark Office*